(12) United States Patent
Clark et al.

(10) Patent No.: US 6,933,283 B2
(45) Date of Patent: Aug. 23, 2005

(54) 11-DEOXY AZALIDE ANTIBACTERIALS

(75) Inventors: Richard Clark, Gurnee, IL (US); Stevan Djuric, Libertyville, IL (US); Zhenkun Ma, Dallas, TX (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/421,577

(22) Filed: Apr. 23, 2003

(65) Prior Publication Data

US 2004/0014953 A1 Jan. 22, 2004

Related U.S. Application Data

(60) Provisional application No. 60/375,325, filed on Apr. 25, 2002.

(51) Int. Cl.⁷ .................... A61K 31/70; C07H 17/08
(52) U.S. Cl. ................ 514/29; 536/7.3; 536/7.4
(58) Field of Search .................. 514/29; 536/7.3, 536/7.4

(56) References Cited

U.S. PATENT DOCUMENTS 5,215,980 A * 6/1993 Jones .................... 514/183

* cited by examiner

*Primary Examiner*—Elli Peselev
(74) *Attorney, Agent, or Firm*—B. Gregory Donner

(57) ABSTRACT

Antibacterial compounds having formula (I)

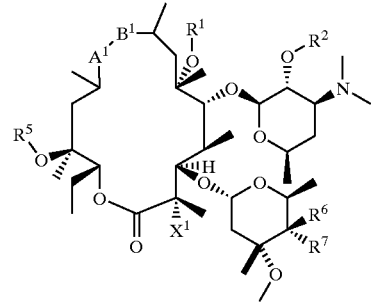

and formula (II)

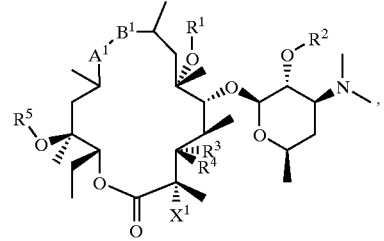

and salts, prodrugs, and salts of prodrugs thereof, processes for making the compounds and intermediates used in the processes, compositions containing the compounds, and methods for prophylaxis or treatment of bacterial infections using the compounds are disclosed.

17 Claims, No Drawings

11-DEOXY AZALIDE ANTIBACTERIALS

This application claims the benefit of co-pending U.S. Application Ser. No. 60/375,325, filed Apr. 25, 2002, the specification of which is hereby incorporated by reference into this application.

TECHNICAL FIELD

This invention is directed to compounds which are useful as antibacterials, processes for making the compounds and intermediates used the processes, compositions containing the compounds, and methods for prophylaxis or treatment of bacterial infections using the compounds.

BACKGROUND OF THE INVENTION

Because the effectiveness of many drugs currently available for prophylaxis or treatment of bacterial infections is being compromised by the emergence of drug-resistant bacteria, novel antibacterias would be beneficial for their therapeutic value and their contribution to the antibacterial arts.

SUMMARY OF THE INVENTION

A first embodiment of this invention, therefore, is directed to compounds which are useful as antibacterials, and salts, prodrugs, and salts of prodrugs thereof, the compounds having formula (I)

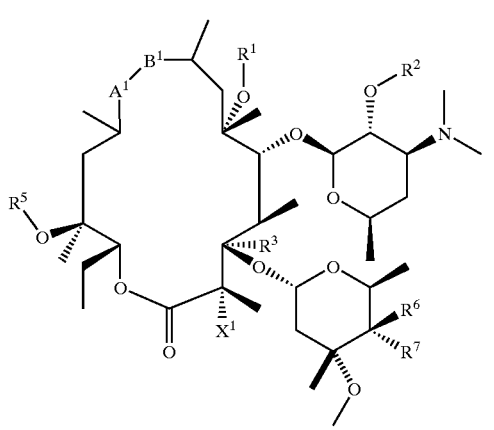

(I)

and formula (II)

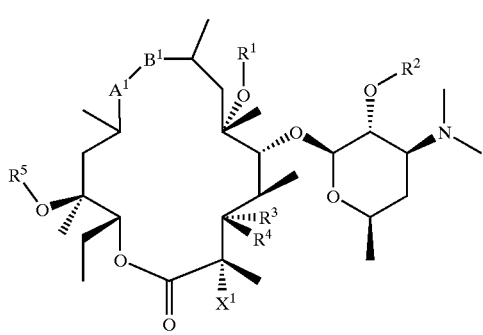

(II)

in which
one of $A^1$ and $B^1$ is —$CH_2$—, and the other is —$N(R^8)$—;
$R^1$ is hydrogen, $C_1$-alkyl, or $R^9$;
$R^2$ is hydrogen or $R^P$, in which $R^P$ is a hydroxyl protecting moiety;

$R^3$ is hydrogen and $R^4$ is —OH, —$OR^{10}$, —$OC(O)OR^{10}$, —$OC(O)NH_2$, —$OC(O)NHR^{11}$, —$OC(O)NR^{11}R^{12}$, —$OCH_2R^{13}$, —$OC(O)OCH_2R^{13}$, —$OC(O)NHCH_2R^{13}$, or —$OC(O)N(CH_2R^{13})_2$; or
$R^3$ and $R^4$ together are =O;
$R^5$ is hydrogen, $R^{14}$, —$C(O)OR^{14}$, —$C(O)NH_2$, —$C(O)NHR^{15}$, —$C(O)NR^{15}R^{16}$, —$CH_2R^{17}$, —$C(O)OCH_2R^{17}$, —$C(O)NHCH_2R^{17}$, or —$C(O)N(CH_2R^{17})_2$;
one of $R^6$ or $R^7$ is hydrogen and the other is —OH, —$OR^{18}$, —$OC(O)R^{18}$, —$OC(O)OR^{18}$, —$OC(O)NH_2$, —$OC(O)NHR^{19}$, —$OC(O)NR^{19}R^{20}$, —$OCH_2R^{21}$, or —$OC(O)OCH_2R^{21}$; or
$R^6$ and $R^7$ together are =O or —$CH_2O$—;
$R^8$ is hydrogen, $R^{22}$, —$C(O)OR^{22}$, —$C(O)NH_2$, —$C(O)NHR^{23}$, —$C(O)NR^{23}R^{24}$, —$CH_2R^{25}$, —$C(O)OCH_2R^{25}$, —$C(O)NHCH_2R^{25}$, or —$C(O)N(CH_2R^{25})_2$; or
$R^1$ is $R^9$, and $R^8$ and $R^9$ together are —$CH_2$— or —$C(O)$—;
$R^{10}$, $R^{14}$, $R^{18}$, and $R^{22}$ are independently alkyl, —($CH_2$)alkenyl, —($CH_2$)alkynyl, alkyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$, —($CH_2$)alkenyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$, or —($CH_2$)alkynyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$;
$R^{11}$, $R^{12}$, $R^{15}$, $R^{16}$, $R^{19}$, $R^{20}$, $R^{23}$, and $R^{24}$, are independently alkyl, cycloalkyl, —($CH_2$)alkenyl, —($CH_2$)alkynyl, cycloalkyl, alkyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$, —($CH_2$)alkenyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$, or —($CH_2$)alkynyl substituted with one substituent selected from the group consisting of cycloalkyl, aryl, heteroaryl, heterocyclyl, —$NH_2$, —NH(alkyl), —NH(alkyl)$_2$, —OH, —O(alkyl), and —$OR^{33}$; or
$R^{10}$ and $R^{11}$ together, $R^{15}$ and $R^{16}$ together, $R^{19}$ and $R^{20}$ together, and $R^{23}$ and $R^{24}$ together are each independently $C_3$–$C_6$-alkylene, $C_5$–$C_6$-alkylene interrupted with one moiety selected from the group consisting of —O—, —NH—, —N(alkyl)-, —S—, —S(O)—, and —$SO_2$—, $C_3$–$C_6$-alkylene substituted with one substituent selected from the group consisting of —OH, —O(alkyl), —$OR^{33}$, =O, —$NH_2$, —NH(alkyl), and —N(alkyl)$_2$, or $C_5$–$C_6$-alkylene interrupted with one moiety selected from the group consisting of —O—, —NH—, —N(alkyl)-, —S—, —S(O)—, and —$SO_2$— and substituted with one substituent selected from the group consisting of aryl, heteroaryl, heterocyclyl, —OH, —O(alkyl), —$OR^{33}$, =O, —$NH_2$, —NH(alkyl), and —N(alkyl)$_2$;
$R^{13}$, $R^{17}$, $R^{21}$, and $R^{25}$ are independently alkyl interrupted with one or two or three moieties independently selected from the group consisting of —O—, —NH—, —N(alkyl)-, —S—, —S(O)—, and —$SO_2$— or alkyl interrupted with one or two or three moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl —OH, —O(alkyl), —$OR^{33}$, =O, —$NH_2$, —NH(alkyl), and —N(alkyl)$_2$;

$R^{33}$ is alkyl substituted with one substituent selected from the group consisting of aryl, —OH, —O(alkyl), —S(alkyl), —S(O)(alkyl), and —SO$_2$(alkyl); and $X^1$ is hydrogen or fluoride.

A second embodiment of this invention is directed to a process for making the compounds.

A third embodiment of this invention is directed to intermediates which are used in the second embodiment.

A fourth embodiment this invention is directed to compositions which are useful for the prophylaxis or treatment of bacterial infections in a fish or a mammal, the compositions comprising a therapeutically effective amount of one or more of the compounds of the first embodiment and an excipient.

A fifth embodiment of this invention is directed to methods for prophylaxis or treatment of bacterial infections in a fish or a mammal comprising administering to the fish or the mammal a therapeutically effective amount of one or more of the compounds of the first embodiment.

DETAILED DESCRIPTION OF THE INVENTION

Compounds of this invention, also referred to as "the compounds," comprise both fixed and variable "moieties," which variable moieties are identified by a capital letter and accompanying numerical or alphabetical superscript, and for which the following terms have the meanings indicated.

"Alkenyl" means monovalent, straight-chain and branched-chain hydrocarbon moieties, having two to eight carbon atoms and at least one carbon-carbon double bond.

Alkenyl moieties include but-1,3-dienyl, butenyl, but-2-enyl, ethenyl, 1-ethylhexen-2-yl, hex-3-enyl, 1-methylbutenyl, 2-methylbutenyl, 1-methylbut-2-enyl, 1-methylbut-1,3-dienyl, pentenyl, pent-2-enyl, and pent-3-enyl, propenyl.

"Alkyl" means monovalent, saturated, straight-chain and branched-chain hydrocarbon moieties, having one to six carbon atoms.

Alkyl moieties include butyl, 1,1,-dimethylethyl, 1,1-dimethylpropyl, 1,2-dimethylpropyl, ethyl, 1-ethylpropyl, 2-ethylpropyl, hexyl, methyl, 2-methylpropyl, 3-methylbutyl, 1-methylpentyl, 2-methylpent-3-yl, and pentyl.

"Alkylene" means divalent, saturated, straight-chain and branched-chain hydrocarbon moieties, having one to eight carbon atoms.

Alkylene moieties include butylene, 1,1,-dimethylethylene, 1,1-dimethylpropylene, 1,2-dimethylpropylene, ethylene, 1-ethylpropylene, 2-ethylpropylene, hexylene, methylene, 2-methylpropylene, 3-methylbutylene, 1-methylpentylene, 2-methylpent-3-ylene, and pentylene.

"Alkynyl" means monovalent, straight-chain and branched-chain hydrocarbon moieties, having two to six carbon atoms and at least one carbon-carbon triple bond.

Alkynyl moieties include ethynyl (acetylenyl), pentynyl, pent-2-ynyl, pent-3-ynyl, pent-4-ynyl, 1-methylbut-2-ynyl, 2-methylbut-3-ynyl, hexynyl, hex-2-ynyl, hex-3-ynyl, hex-4-ynyl, 1-methyl-pent-2-ynyl, 1-methylenepent-3-ynyl, 1-methyl-pent-2,4-diynyl, and prop-2-ynyl (propargyl).

"Aryl" means monovalent, unsubstituted and substituted phenyl moieties, attached through a carbon atom, and unfused or fused with another phenyl moiety or a cycloalkyl, cycloalkenyl, heteroaryl, heterocyclyl, naphthyl, or saturated part of an indanyl moiety.

Phenyl moieties fused with phenyl, naphthyl, or the saturated part of an indanyl moieties are unsubstituted and substituted naphthyl, anthracen-(1- to 4-)yl, or fluoren-(1- to 4-)yl, respectively.

Phenyl moieties fused with cycloalkyl moieties are unsubstituted and substituted indan-(4- to 7-)yl and 1,2,3,4-tetrahydronaphth-(5- to 8-)yl.

Phenyl moieties fused with cycloalkenyl moieties are unsubstituted and substituted inden-(4- to 7-)yl, 1,2-dihydronaphth-(5- to 8-)yl and 1,2-dihydronaphth-(5- to 8-)yl.

Phenyl moieties fused with heteroaryl moieties include unsubstituted and substituted benzimidazol-(4- to 7-)yl, 1-benzofuran-(4- to 7-)yl, 1,2-benzisothiazol-(4- to 7-)yl, benzthiazol-(4- to 7-)yl, 1-benzothiophen-(4- to 7-)yl, cinnolin-(5- to 8-)yl, indol-(4- to 7-)yl, isoquinolin-(5- to 8-)yl, phthalazin-(5- to 8-)yl, quinazolin-(5- to 8-)yl, quinolin-(5- to 8-)yl, and quinoxalin-(5- to 8-)yl.

Phenyl moieties fused with heterocyclyl moieties include unsubstituted and substituted 1,3-benzodiox-(4- to 7-)yl, 1,4-benzodiox-(5- to 8-)yl, 1,3-dihydro-2-benzofuran-(4- to 7-)yl, 2,3-dihydro-1-benzofuran-(4- to 7-)yl, 1,3-dihydro-2-benzothiophen-(4- to 7-)yl, 2,3-dihydro-1-benzothiophen-(4- to 7-)yl, and indolin-(4- to 7-)yl.

"Cycloalkyl" means monovalent, unsubstituted and substituted, saturated cyclic hydrocarbon moieties, having three to six carbon atoms.

Cycloalkyl moieties are unsubstituted and substituted cyclopropyl, cyclobutyl, cyclopentyl, and cyclohexyl.

"Cycloalkenyl" means means monovalent, unsubstituted and substituted, cyclic hydrocarbon moieties having four to six carbon atoms and at least one carbon-carbon double bond.

Cycloalkenyl moieties are unsubstituted and substituted 1,3-cyclohexadienyl, 1,4-cyclohexadienyl, cyclohexenyl, cyclopentadienyl, and cyclopentenyl.

"Halo" means fluoro (—F), chloro (—Cl), bromo (—Br), and iodo (—I) moieties.

"Heteroaryl" means monovalent, aromatic, unsubstituted and substituted five-membered ring moieties having two double bonds and (a) one oxygen or one sulfur atom, (b) one, two, three, or four nitrogen atoms, or (c) one or two nitrogen atoms and one oxygen or one sulfur atom and the remaining atoms are carbon atoms, each of which is attached through a carbon atom or a nitrogen atom; and monovalent six-membered ring moieties having three double bonds and one or two or three nitrogen atoms and the remaining atoms are carbon atoms, attached through a carbon atom; in which the foregoing heteroaryl moieties are unfused or fused with another heteroaryl moiety or an aryl moiety.

Five-membered heteroaryl moieties are unsubstituted and substituted furanyl, imidazolyl, isothiazolyl, isoxazolyl, 1,2,3-oxadiazolyl, oxazolyl, pyrazolyl, pyrrolyl, tetraazolyl, 1,3,4-thiadiazolyl, thiazolyl, thiophenyl (thienyl), 2H-tetraazolyl, and 1,2,3-triazolyl.

Five-membered heteroaryl moieties fused with aryl moieties include unsubstituted and substituted benzimidazol-(1- or 2-)yl, 1-benzofuran-(2- to 3-)yl, 1,2-benzisothiazol-3-yl, benzthiazol-2-yl, 1-benzothiophen-(2- to 3-)yl, cinnolin-(3- or 4-)yl, indol-(1- to 3-)yl, isoquinolin-(1-, 3-, or 4-)yl, phthalazin-(1- or 4-)yl, quinazolin-(2- or 4-)yl, quinolin-(2- to 4-)yl, and quinoxalin-(2- or 3-)yl.

Five-membered heteroaryl moieties fused with other five-membered heteroaryl moieties include unsubstituted and substituted [1,3]thiazolo[4,5-d][1,3]oxazolyl, [1,3]thiazolo

[4,5-d][1,3]thiazolyl, thieno[3,2-d][1,3]oxazolyl, thieno[3,2-d][1,3]thiazolyl, and thieno[2,3-b]thiophenyl.

Five-membered heteroaryl moieties fused with six-membered heteroaryl moieties include unsubstituted and substituted furo[2,3-b]pyridin-(2- or 3-)yl, 3H-imidazo[4,5-b]pyridin-(2- or 3-)yl, [1,3]thiazolo[4,5-b]pyrazin-2-yl, [1,3]thiazolo[4,5-b]pyridin-2-yl, and thieno[2,3-b]pyridin-(2- or 3-)yl.

Six-membered heteroaryl moieties are unsubstituted and substituted pyrazinyl, pyridazinyl, pyridyl, pyrimidinyl, and 1,3,5-triazinyl.

Six-membered heteroaryl moieties fused with aryl moieties include unsubstituted and substituted cinnolin-(3- or 4-)yl, isoquinolin-(1-, 3-, or 4-)yl, phthalazin-(1- or 4-)yl, quinazolin-(2- or 4-)yl, quinolin-(2- to 4-)yl, and quinoxalin-(2- or 3-)yl.

Six-membered heteroaryl moieties fused with five-membered heteroaryl moieties include unsubstituted and substituted furo[2,3-b]pyridin-(4- to 6-)yl, 3H-imidazo[4,5-b]pyridin-(5- to 7-)yl, [1,3]thiazolo[4,5-b]pyrazin-(5- or 6-)yl, [1,3]thiazolo[4,5-b]pyridin-(5- to 7-)yl, and thieno[2,3-b]pyridin-(4- to 6-)yl.

Six-membered heteroaryl moieties fused with other six-membered heteroaryl moieties include unsubstituted and substituted 1,5-naphthyridinyl, 1,7-naphthyridinyl, 1,8-naphthyridinyl, pteridinyl, pyridazino[4,5-d]pyridazinyl, pyrido[2,3-d]pyridazinyl, and pyrido[3,4-d]pyridazinyl.

"Heterocyclyl" means (a) monovalent, non-aromatic, unsubstituted and substituted four-membered ring moieties having one nitrogen, oxygen, or sulfur atom and the remaining atoms are carbon atoms, zero double bonds, attached through a carbon atom or a nitrogen atom, (b) monovalent, non-aromatic, unsubstituted and substituted five-membered ring moieties having one or two nitrogen, oxygen, or sulfur atoms and the remaining atoms are carbon atoms, and zero or one double bonds, attached through a carbon atom or a nitrogen atom, and (c) monovalent, non-aromatic, unsubstituted and substituted six-membered ring moieties having one or two or three nitrogen, oxygen, or sulfur atoms and the remaining atoms are carbon atoms, and zero, one, or two double bonds, attached through a carbon atom or a nitrogen atom.

Four-membered heterocyclyl moieties are unsubstituted and substituted oxetane, thietane, and azetidine.

Five-membered heterocyclyl moieties include unsubstituted and substituted 1,4-dioxanyl, 1,3-dioxolanyl, imidazolidinyl, 2-imidazolinyl, 4,5-dihydroisoxazolyl, pyrazolidinyl, 2-pyrazolinyl, pyrrolidinyl, 2-pyrrolinyl, 3-pyrrolinyl, and 2H-pyrrolyl.

Six-membered heterocyclyl moieties include unsubstituted and substituted 1,3-dithianyl, 1,4-dithianyl, morpholinyl, piperidinyl, piperazinyl, pyranyl, 2H-pyranyl, 4H-pyranyl, and thiomorpholinyl.

Substituted aryl and heteroaryl moieties are those moieties substituted with one, two, three, four, or five substituents independently selected from the group consisting of alkyl, alkenyl, alkynyl, cycloalkyl, halo, —CN, —OH, —SH, —NH$_2$, —NO$_2$, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and R$^{40}$, in which R$^{30}$ is alkyl or alkyl substituted with one substituent selected from the group consisting of halo, —O(alkyl), and —S(alkyl), and R$^{40}$ is furyl, imidazolyl, indazolidinyl, isoquinolyl, isothiazolyl, isoxazolyl, morpholinyl, naphthyl, naphthyridyl, 1,2,3-oxadiazolyl, oxazolyl, phenyl, piperidinyl, piperazinyl, pyrazinyl, pyrazolyl, pyridyl, pyrimidinyl, pyrrolidinyl, pyrrolyl, quinazolyl, quinolyl, quinoxalyl, tetrazolyl, 1,2,3-thiadiazolyl, 1,3,4-thiadiazolyl, thiazolyl, thienyl, 1,2,3-triazolyl, or thiomorpholinyl, in which each R$^{40}$ moiety is unsubstituted or substituted with one or two or three substituents independently selected from the group consisting of alkyl, alkenyl, alkynyl, cycloalkyl, halo, =O, —CN, —OH, —SH, —NO$_2$, —CF$_3$, —CH$_2$CF$_3$, —CF$_2$CF$_3$, —OCF$_3$, —OCH$_2$CF$_3$, —OCF$_2$CF$_3$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), and —SO$_2$N(alkyl)$_2$.

Substituted cycloalkyl, cycloalkenyl, and heterocyclyl moieties are those moieties substituted with one or two or three substituents independently selected from the group consisting of alkyl, phenyl, halo, —CN, —OH, —NH$_2$, —CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), and —C(O)N(alkyl)$_2$, in which the phenyl is unsubstituted or substituted with one or two or three substituents independently selected from the group consisting of halo, —CN, —OH, —NH$_2$, and —CF$_3$.

"Hydroxyl protecting moiety" means selectively introducible and removable moieties which protect —OH moieties against undesirable side reactions. Hydroxyl protecting moieties include 4-nitrobenzyloxycarbonyl, 4-bromobenzyloxycarbonyl, 4-methoxybenzyloxycarbonyl, 3,4-dimethoxybenzyloxycarbonyl, tert-butoxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, allyloxycarbonyl, acetyl, chloroacetyl, dichloroacetyl, trichloroacetyl, trifluoroacetyl, methoxyacetyl, phenoxyacetyl, pivaloyl, propionyl, 2-methylpropionyl, benzoyl, tert-butyl, 2,2,2-trichloroethyl, 2-trimethylsilylethyl, 1,1-dimethyl-2-propenyl, 3-methyl-3-butenyl, para-methoxybenzyl, 3,4-dimethoxybenzyl, diphenylmethyl, triphenylmethyl, tetrahydrofuryl, benzyloxymethyl, 2-methoxyethoxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

These variable moieties may combine to provide a sixth embodiment of this invention, which embodiment is directed to compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen, R$^{14}$, —C(O)OR$^{14}$, —C(O)NH$_2$, —C(O)NHR$^{15}$, —C(O)NR$^{15}$R$^{16}$; one of R$^6$ or R$^7$ is hydrogen and the other is —OH; or R$^6$ and R$^7$ together are =O; R$^8$ is hydrogen, R$^{22}$, —C(O)OR$^{22}$, —C(O)NH$_2$, —C(O)NHR$^{23}$, or —C(O)NR$^{23}$R$^{24}$; or R$^1$ is R$^9$, and R$^8$ and R$^9$ together are —CH$_2$— or —C(O)—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$, —(CH$_2$)alkenyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$, or —(CH$_2$)alkynyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$; R$^{15}$, R$^{16}$, R$^{23}$, and R$^{24}$ are independently alkyl, cycloalkyl, —(CH$_2$)alkenyl, —(CH$_2$)alkynyl, cycloalkyl, alkyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$, —(CH$_2$)alkenyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$, or —(CH$_2$)alkynyl substituted with one substituent selected from the group consisting of cycloalkyl, aryl, heteroaryl, heterocyclyl, —NH$_2$, —NH(alkyl), —NH(alkyl)$_2$, —OH, —O(alkyl), and —OR$^{33}$; R$^{33}$ is alkyl substituted with one substituent selected from the group consisting of aryl, —OH, —O(alkyl), —S(alkyl), —S(O)(alkyl), and —SO$_2$(alkyl); and X$^1$ is hydrogen or fluoride;

compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen or R$^{14}$; one of R$^6$ or R$^7$ is hydrogen and the other is —OH; or R$^6$ and R$^7$ together are =O; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride;

compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen or R$^{14}$; one of R$^6$ or R$^7$ is hydrogen and the other is —OH; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride;

compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; R$^5$ is hydrogen or R$^{14}$; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride;

compounds having formula (I) or formula (II), and salts, prodrugs, and salts of prodrugs, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; R$^5$ is hydrogen; R$^6$ is hydrogen; R$^7$ is —OH; R$^8$ is hydrogen, R$^{22}$ or —C(O)OR$^{22}$; or R$^1$ is R$^9$, and R$^8$ and R$^9$ together are —CH$_2$—; R$^{22}$ is alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride;

compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; R$^5$ is hydrogen; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{22}$ is alkyl, —(CH$_2$)alkenyl, alkyl substituted with one substituent selected from the group consisting of aryl, heteroaryl, and heterocyclyl, or —(CH$_2$)alkenyl substituted with one substituent selected from the group consisting of aryl and heteroaryl; and X$^1$ is hydrogen or fluoride; and compounds having formula (I) or formula (II), and salts, prodrugs, and salts of prodrugs thereof, in which one of A$^1$ and B$^1$ is —CH$_2$—, and the other is —N(R$^8$)—; R$^1$ is hydrogen or R$^9$; R$^2$ is hydrogen or R$^P$, in which R$^P$ is a hydroxyl protecting moiety; $R^3$ is hydrogen and $R^4$ is —OH; $R^5$ is hydrogen; $R^6$ is hydrogen; $R^7$ is —OH; $R^8$ is hydrogen, methyl, ethyl, phenylmethyl, (pyridin-3-yl)methyl, prop-2-enyl, 3-(quinolin-3-yl)-prop-2-enyl, 3-(isoquinolin-3-yl)-prop-2-enyl, 3-(5-(2-methyl-2H-tetrazol-5-yl)-thien-2-yl)-prop-2-enyl, 3-(5-(pyrimidin-2-yl)-thien-2-yl)-prop-2-enyl, 3-(5-(pyridin-2-yl)-thien-2-yl)-prop-2-enyl, (3-(4-fluorophenyl)-4,5-dihydroisoxazol-5-yl)methyl, (3-(phenyl)-4,5-dihydroisoxazol-5-yl)methyl, (3-(pyridin-2-yl)-4,5-dihydroisoxazol-5-yl)methyl, or (phenylmethoxy)carbonyl; or $R^1$ is $R^9$, and $R^8$ and $R^9$ together are —$CH_2$—; and $X^1$ is hydrogen or fluoride.

Specific examples of an $A^1$ moiety for compounds having formula (I) are —$CH_2$— and —$N(R^8)$—.

Specific examples of a $B^1$ moiety for compounds having formula (I) are —$N(R^8)$— and —$CH_2$—.

A specific example of an $R^1$, $R^2$, $R^3$, $R^5$, and $R^6$ moiety for compounds having formula (I) is hydrogen.

Another specific example of an $R^1$ moiety for compounds having formula (I) is $R^9$, in which $R^9$ taken together with $R^8$ forms a —$CH_2$— moiety.

A specific example of an $R^7$ moiety for compounds having formula (I) is —OH.

Specific examples of an $R^8$ moiety for compounds having formula (I) are 3-quinolin-3-ylprop-2-enyl, (3-(4-fluorophenyl)-4,5-dihydroisoxazol-5-yl)methyl, (phenylmethoxy)carbonyl, hydrogen, methyl, and prop-2-enyl.

A specific example of an $X^1$ moiety for compounds having formula (I) is hydrogen.

These specific moieties of the compounds may combine with the fixed moieties thereof to form a seventh embodiment of this invention, which embodiment is directed to compounds, and salts, prodrugs, and salts of prodrugs thereof, having formula (I), in which one of $A^1$ and $B^1$ is —$CH_2$—, and the other is —$N(R^8)$—; $R^1$ is hydrogen or $R^9$; $R^2$, $R^5$, and $R^6$ are hydrogen; $R^7$ is —OH; $R^8$ is hydrogen, $R^{22}$, or —$C(O)OR^{22}$; or $R^1$ is $R^9$, and $R^8$ and $R^9$ together are —$CH_2$—; $R^{22}$ is alkyl, —($CH_2$)alkenyl, alkyl substituted with one substituent selected from the group consisting of phenyl and 4,5-dihydroisoxazolyl, in which the 4,5-dihydroisoxazolyl is substituted with phenyl, and the phenyl is further substituted with one halo substituent, or —($CH_2$) alkenyl substituted with pyridyl, in which the pyridyl is fused with phenyl; and $X^1$ is hydrogen;

compounds, and salts, prodrugs, and salts of prodrugs thereof, having formula (I) in which one of $A^1$ and $B^1$ is —$CH_2$—, and the other is —$N(R^8)$—; $R^1$ is hydrogen or $R^9$; $R^2$, $R^5$, and $R^6$ are hydrogen; $R^7$ is —OH; $R^8$ is hydrogen, $R^{22}$, or —$C(O)OR^{22}$; or $R^1$ is $R^9$, and $R^8$ and $R^9$ together are —$CH_2$—; $R^{22}$ is $C_1$-alkyl, —($CH_2$)—$C_2$-alkenyl, $C_1$-alkyl substituted with one substituent selected from the group consisting of phenyl and 4,5-dihydroisoxazolyl, in which the 4,5-dihydroisoxazolyl is substituted with phenyl, and the phenyl is further substituted with one halo substituent, or —($CH_2$)—$C_2$-alkenyl substituted with pyridyl, in which the pyridyl is fused with phenyl; and $X^1$ is hydrogen;

compounds, and salts, prodrugs, and salts of prodrugs thereof, having formula (I), in which $A^1$ is —$N(R^8)$—, $B^1$ is —$CH_2$—; $R^1$, $R^2$, $R^5$, and $R^6$ are hydrogen; $R^7$ is —OH; $R^8$ is hydrogen, methyl, prop-2-enyl, (3-(4-fluorophenyl)-4,5-dihydroisoxazol-5-yl)methyl, 3-(quinolin-3-yl)-prop-2-enyl, or (phenylmethoxy)carbonyl; and $X^1$ is hydrogen;

compounds having formula (I), and salts, prodrugs, and salts of prodrugs therof, in which $A^1$ is —$CH_2$—, $B^1$ is —$N(R^8)$—; $R^1$, $R^2$, $R^5$, and $R^6$ are hydrogen; $R^7$ is —OH; $R^8$ is hydrogen, methyl, prop-2-enyl, (3-(4-fluorophenyl)-4,5-dihydroisoxazol-5-yl)methyl, 3-(quinolin-3-yl)-prop-2-enyl, or (phenylmethoxy)carbonyl; and $X^1$ is hydrogen; and compounds having formula (I), and salts, prodrugs, and salts of prodrugs thereof, in which one of $A^1$ and $B^1$ is —$CH_2$—, and the other is —$N(R^8)$—; $R^1$ is $R^9$; $R^2$ $R^5$, and $R^6$ are hydrogen; $R^7$ is —OH; $R^8$ and $R^9$ together are —$CH_2$—; and $X^1$ is hydrogen; and compounds, and salts, prodrugs, and salts of prodrugs thereof, which are (2R,3S,5S,8R,10S,11R,12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8S,10S,11R,12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5(R or S),8(R or S),10S,11R, 12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-7-azacyclopentadecan-13-yl 2,6-dideoxy-3-C-methyl-3-O-methyl-α-L-ribo-hexopyranoside;

(2R,3S,5S,8S,10S,11R,12S, 13S,14R)-2-ethyl-3,10-dihydroxy-3,5,6,8,10,12,14-heptamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2S,4S,5R,8R,9S,10S,11R, 12R,14R)-5-ethyl-4-hydroxy-2,4,8,10,12,14-hexamethyl-7-oxo-11-((3,4,6-trideoxy-3-(dimethylamino)-β-D-xylo-hexopyranosyl)oxy)-6,17-dioxa-1-azabicyclo[10.3.2]heptadec-9-yl 2,6-dideoxy-3-C-methyl-3-O-methyl-α-L-ribo-hexopyranoside;

(2R,3S,5S,8R,10S,11R,12S,13S, 14R)-6-allyl-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S, 14R)-2-ethyl-3,10-dihydroxy-3,5,8,10,12,14-hexamethyl-15-oxo-6-((2E/Z)-3-(3-quinolinyl)-2-propenyl)-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S,14R)-2-ethyl-6-((3-(4-fluorophenyl)-4,5-dihydroisoxazol-5-yl)methyl)-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside; and benzyl (2R,3S,5S,8R,10S,11R,12S,13S, 14R)-13-((2,6-dideoxy-3-C-methyl-3-O-methyl-α-L-ribo-hexopyranosyl)oxy)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecane-6-carboxylate.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13–10. Compounds having asymmetrically substituted carbon atoms with equal amounts of R and S configurations are racemic at those carbon atoms. Atoms with an excess of one configuration over the other are assigned the configuration which is present in the higher amount, preferably an excess of about 85%–90%, more preferably an excess of about 95%–99%, and still more preferably an excess greater than about 99%. Accordingly, this invention is meant to embrace all stereoisomers of the compounds including racemic mixtures, enantiomers, mixtures of enantiomers, diastereomers, and mixtures of diastereomers.

Individual stereoisomers of the compounds may be prepared by any one of a number of methods known in the art. These methods include stereospecific synthesis, chromatographic separation of diastereomers, chromatographic resolution of enantiomers, enzymatic resolution, and converting of enantiomers in an enantiomeric mixture to diastereomers, chromatographically separating the diastereomers and regenerating of the individual enantiomers.

Stereospecific syntheses involve the use of appropriate chiral starting materials and synthetic reactions which do not cause racemization or inversion of stereochemistry at the chiral centers.

Diastereomeric mixtures of compounds resulting from a synthetic reaction can be separated by chromatographic techniques which are known in the art.

Chromatographic resolution of enantiomers can be accomplished on commercially available, chiral chromatography resins. In practice, a solution of the racemate is loaded onto a column of chiral stationary phase, and the enantiomers are separated by high performance liquid chromatography.

Enzymes, such as esterases, phosphatases and lipases, may also be useful for resolution of derivatives of the enantiomers in an enantiomeric mixture. For example, an ester derivative of a carboxyl group of the compounds to be separated can be prepared. Certain enzymes will selectively hydrolyze only one of the enantiomers in the mixture; and the resulting enantiomerically pure acid can be separated from the unhydrolyzed ester.

Resolution of enantiomers may also be accomplished by converting enantiomers to diastereomers by reacting the former and chiral auxiliaries. The resulting diastereomers may then be separated by column chromatography. This technique is especially useful for compounds containing —$CO_2H$, —N(H)—, —OH, or —SH moieties, which moieties may form a salt or covalent bond with the chiral auxiliary. Chirally pure amino acids, organic carboxylic acids, or organosulfonic acids are especially useful as chiral auxiliaries. Once the diastereomers have been separated by chromatography, the individual enantiomers can be regenerated. Frequently, the chiral auxiliary can be recovered and reused.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds may also exist as an equilibrium mixture of Z or E configurations.

Compounds of this invention containing —$CO_2H$, —N(H)—, —OH, or —SH moieties may have attached thereto prodrug-forming moieties. The prodrug-forming moieties are removed by metabolic processes and the compounds having the freed —$CO_2H$, —N(H)—, —OH, or —SH moieties are released in vitro or in vivo. Prodrugs are useful for adjusting such pharmacokinetic properties of the compounds as solubility and/or hydrophobicity, absorption in the gastrointestinal tract, bioavailability, tissue penetration, and rate of clearance.

Compounds of this invention may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, undecanoate, and their equivalent salts of the compounds and prodrugs thereof are contemplated as being embraced by this invention. When the compounds contain carboxylic acids, basic addition salts may be prepared therefrom by reaction with a base such as the hydroxide, carbonate, and bicarbonate of cations such as lithium, sodium, potassium, calcium, and magnesium.

Compounds of this invention may be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, aluminum hydroxide, benzyl alcohol, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, Ringer's solution, talc, tragacanth, water, safflower oil, sesame oil, sodium carboxymethyl cellulose, sodium lauryl sulfate, sodiumphosphate salts, soybean oil, sucrose, tetrahydrofurfuryl alcohol, and mixtures thereof. Excipients for ophthalmically and orally administered compounds in liquid dosage forms include benzyl alcohol, benzyl benzoate, 1,3-butylene glycol, castor oil, corn oil, cottonseed oil, ethanol, ethyl acetate, ethyl carbonate, fatty acid esters of sorbitan, germ oil, groundnut oil, glycerol, isopropanol, olive oil, polyethylene glycols, propylene glycol, sesame oil, tetrahydrofurfuryl alcohol, water, and mixtures thereof. Excipients for osmotically administered compounds include chlorofluorohydrocarbons, ethanol, isopropanol, water, and mixtures thereof. Excipients for parenterally administered compounds include 1,3-butanediol, castor oil, corn oil, cottonseed oil, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for rectally and vaginally administered compounds include cocoa butter, polyethylene glycol, wax, and mixtures thereof.

Compounds of this invention may be administered orally, ophthalmically, osmotically, parenterally (subcutaneously, intramuscularly, intrasternally, intravenously), rectally, topically, transdermally, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups.

Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous suspensions, which suspensions comprise crystalline, amorphous, or otherwise insoluble forms of the compounds. Rectally and vaginally administered compounds may be administered as creams, gels, lotions, ointments, and pastes.

Therapeutically effective amounts of compounds of this invention depend on the recepient of treatment, the disorder being treated and the severity thereof, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

To determine antibacterial activity of compounds of this invention, twelve petri dishes, each containing successive aqueous dilutions of test compounds in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing Streptococcus strains), co-incubated at 35–37° C. for 20–24 hours with a control plate having no compound, and inspected visually to provide the minimum inhibitory concentration (MIC), in µg/mL, by which is meant the lowest concentration of the test compound which yielded no growth, a slight haze, or sparsely isolated colonies on the inoculums spot as compared to growth in the control plate.

TABLE 1

| Microorganism | Code |
| --- | --- |
| Staphylococcus aureus NCTC10649M | AA |
| Staphylococcus aureus A5177 | BB |
| Staphylococcus aureus PIU 2043 | CC |

TABLE 1-continued

| Microorganism | Code |
| --- | --- |
| Staphylococcus aureus 1775 | DD |
| Streptococcus pyrogenes EES61 | EE |
| Streptococcus pyrogenes 930 | FF |
| Streptococcus pyrogenes PIU 2548 | GG |
| Streptococcus pneumoniae ATCC 6303 | HH |
| Streptococcus pneumoniae 5979 | JJ |
| Streptococcus pneumoniae 5649 | KK |
| Enterococcus faecalis PIU 1967 | LL |
| Enterococcus faecium GYR 1632 | MM |
| Moraxella catarrhalis 2604 | NN |
| Haemophilus influenzae GYR 1435 | PP |
| Escherichia coli JUHL | QQ |

Compounds of this invention displayed antibacterial activity in the range of about 0.03 µg/mL to greater than about 128 µg/mL against the microorganisms listed in Table 1. This antibacterial activity demonstrates the utility of the compounds as antibacterials.

It is meant to be understood that certain metabolites of compounds of this invention, which metabolites are produced by in vitro or in vivo metabolic processes, would also be useful as antibacterials and are meant to be embraced by this invention.

It is also meant to be understood that certain precursor compounds, which precursor compounds may be metabolized in vitro or in vivo to form compounds of this invention, are meant to be embraced by this invention.

Compounds of this invention may also be prepared by synthetic chemical processes, examples of which synthetic chemical processes, and intermediates used in the processes, are shown hereinbelow. It is meant to be understood that the order of the steps in the processes may be varied, equivalent reagents, solvents, and reaction conditions may be substituted for those specifically mentioned, and vulnerable moieties may be protected and deprotected during the process.

Abbreviations used are CBZ-NOS for N-(benzyloxycarbonyloxy)succinimide, DMF for N,N-dimethylformamide, DME for 1,2-dimethoxyethane, and THF for tetrahydrofuran.

SCHEME 1

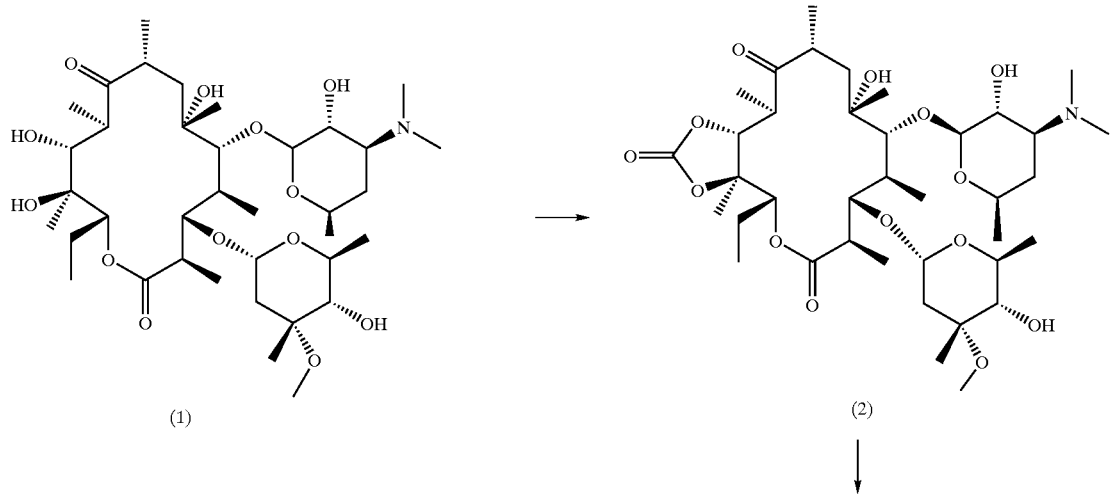

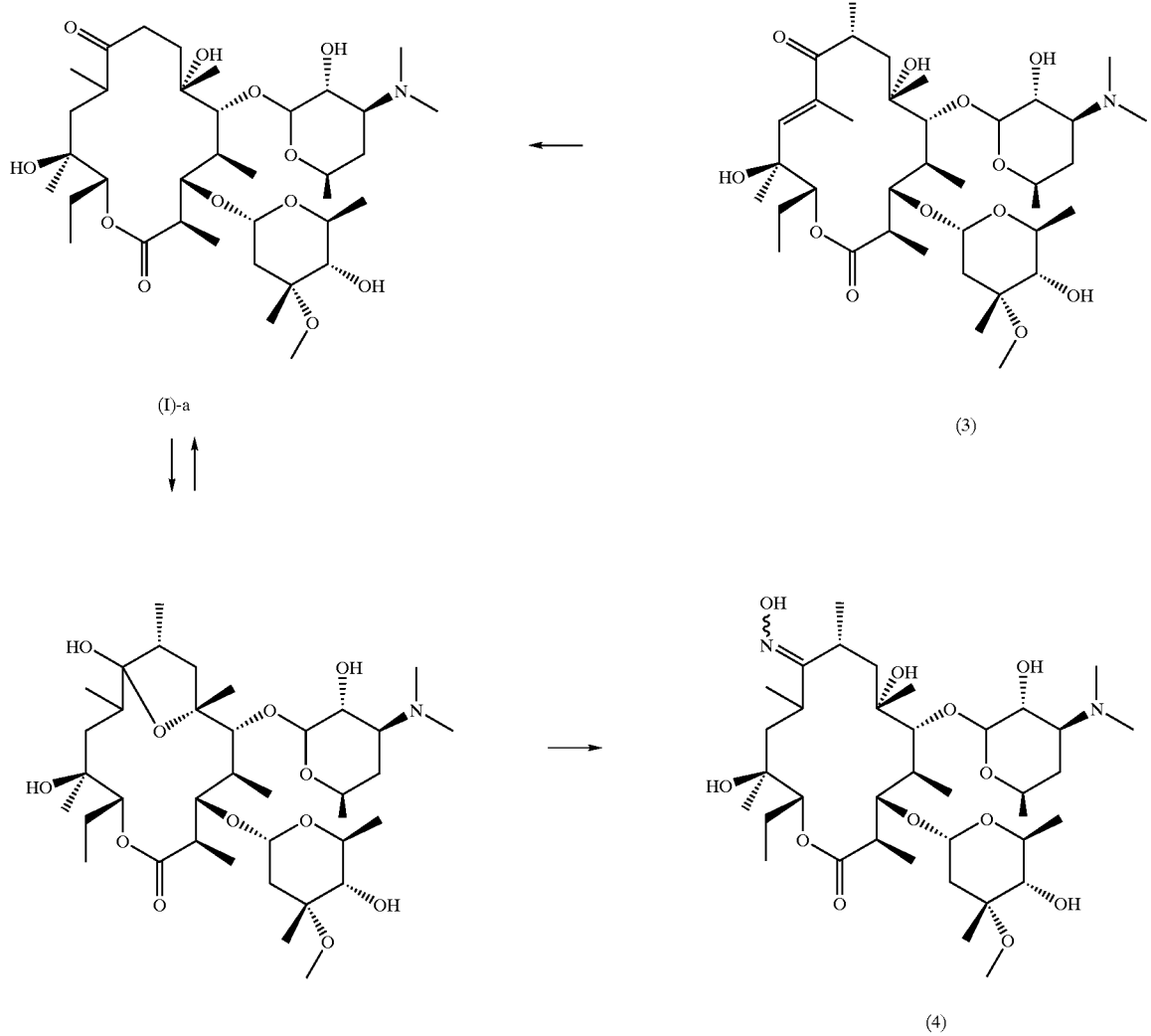

Erythromycin A (1) may be converted to the compound having formula (2) by reacting the former, a carbonate-forming agent, and a first base.

Carbonate-forming agents include dimethyl carbonate, diethyl carbonate, ethylene carbonate, and phosgene.

First bases include pyridine, diisopropylethylamine, triethylamine, and potassium carbonate.

The reaction is typically conducted in solvents such as benzene, toluene, and xylene, at temperatures of between about 50° C. and 120° C., over about 1 to 18 hours.

The compound having formula (2) may be converted to the compound having formula (3) by reacting the former and tetramethylguanidine in solvents such as THF, DME, DMF, and toluene, at temperatures of between about 50° C. and about 120° C., over about 10 to 24 hours.

The compound having formula (3) may be converted to the compound having formula (I)-a by reacting the former, hydrogen and 10% palladium on carbon in solvents such as methanol, ethanol, isopropanol, ethyl acetate, and mixtures thereof, at temperatures of between about 25° C. and about 50° C., over about 10 to 24 hours.

The compound having formula (I)-a may be converted to the compound having formula (4) by reacting the former, hydroxylamine or the hydrochloride salt thereof, and a second base.

Second bases include pyridine, diisopropylethylamine, and triethylamine. The reaction is typically conducted in solvents such as methanol, ethanol, isopropanol, and mixtures thereof, at temperatures of between about 25° C. and about 75° C., over about 10 to about 24 hours.

SCHEME 2

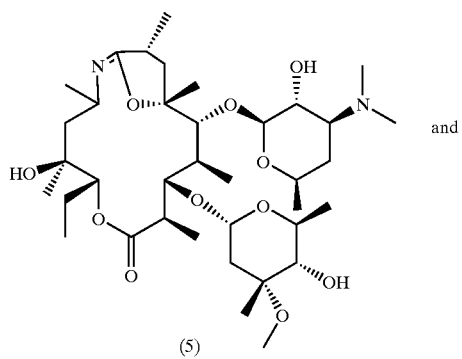

and

-continued

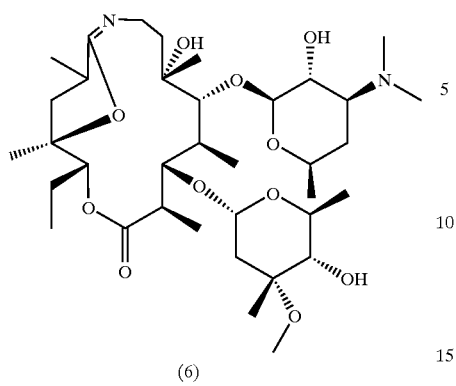

(6)

The compound having formula (5) may be converted to the compounds having formula (4) and formula (6) by reacting the former and compounds having formula $R^A SO_2 Cl$, in which $R^A$ is methyl, ethyl, isopropyl, phenyl, naphthyl, phenyl substituted with one, two, or three substituents independently selected from the group consisting of methyl, ethyl, isopropyl, halo, —N(alkyl)$_2$, —NO$_2$, —CF$_3$, and —OCF$_3$, or naphthyl substituted with one or two or three substituents independently selected from the group consisting of methyl, ethyl, isopropyl, halo, —N(alkyl)$_2$, —NO$_2$, —CF$_3$, and —OCF$_3$, and a third base.

Third bases include pyridine, diisopropylethylamine, triethylamine, sodium carbonate, sodium bicarbonate, and potassium carbonate. The reaction is typically conducted in solvents such as acetone, water, tetrahydrofuran, dichloromethane, and mixtures thereof, at temperatures of between about 0° C. and about 30° C., over about 10 to about 24 hours.

SCHEME 3

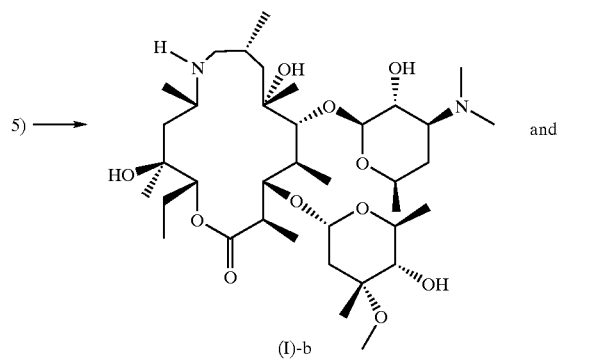

(I)-b

-continued

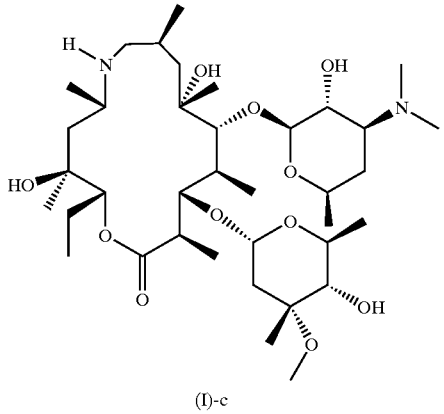

(I)-c

The compound having formula (5) may be converted to compounds having formula (I)-b and (I)-c by reacting the former, hydrogen and platinum oxide in acetic acid, at temperatures of between about 15° C. and about 35° C., over about 10 to about 24 hours.

SCHEME 4

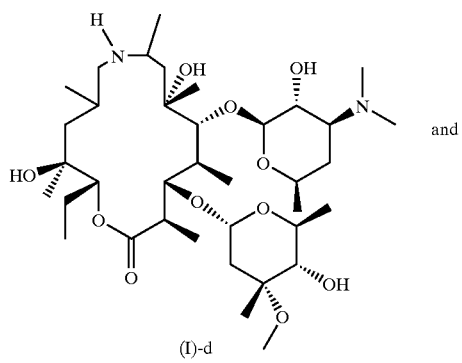

(I)-d and

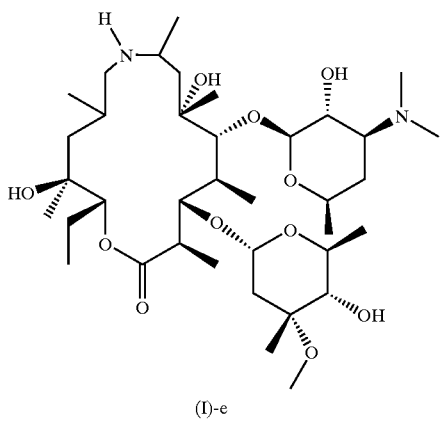

(I)-e

The compound having formula (6) may be converted to the compounds having formula (I)-d and (I)-e by reacting the former, hydrogen and platinum oxide in acetic acid at temperatures of between about 15° C. and about 35° C., over about 10 to about 24 hours.

The compounds and processes of this invention will be better understood in connection with the following examples.

EXAMPLE 1

A mixture of erythromycin A (50 g), ethylene carbonate (59.7 g), and $K_2CO_3$ (28.8 g) in toluene (150 mL) and THF (150 mL) was stirred at 103° C. for 8 hours and cooled, treated with toluene (300 mL), washed with 10% $NaHCO_3$ and brine, and dried ($Na_2SO_4$), filtered, and concentrated.

EXAMPLE 2

A mixture of EXAMPLE 1 (27.9 g) and tetramethylguanidine (23 mL) in DME (140 mL) was stirred at reflux for 18 hours and cooled, treated with dichloromethane, washed with water and brine, and dried ($Na_2SO_4$), filtered, concentrated, triturated twice with hot diethyl ether, and filtered.

EXAMPLE 3

A mixture of EXAMPLE 2 (100 mg) and 10% palladium on carbon (100 mg) in methanol (3 mL) at 25° C. was stirred under hydrogen (1 atm) for 17 hours, filtered through diatomaceous earth (Celite®), and concentrated.

EXAMPLE 4

A mixture of EXAMPLE 3 (400 mg), hydroxylamine hydrochloride (192.5 mg), and triethylamine (225 µL) in methanol (1 mL) was stirred at reflux for 22 hours and cooled, treated with dichloromethane, washed with 5% $Na_2CO_3$ and brine, dried ($Na_2SO_4$), filtered, concentrated, and flash chromatographed on silica gel with 98:1.5:1 dichloromethane/methanol/ammonium hydroxide.

EXAMPLE 5 and EXAMPLE 6

A mixture of EXAMPLE 4 (1 g) in acetone (11 mL) at 0° C. was treated simultaneously with toluenesulfonyl chloride (781 mg) in acetone (5 mL) and $NaHCO_3$ (689 mg) in water (10 mL) over 1.5 hours, stirred for 14 hours at 25° C., treated with dichloromethane (150 mL), and washed with water (30 mL). The water layer was adjusted to pH 4 with 5% $KH_2PO_4$, extracted with dichloromethane, adjusted to pH 8–9 with 5% $NaHCO_3$, and extracted with dichloromethane. The combined extracts were washed with brine, dried ($Na_2SO_4$), filtered, concentrated, and flash chromatographed on silica gel with 98:1:1 to 96:3:1 dichloromethane/methanol/ammonium hydroxide.

EXAMPLE 7 and EXAMPLE 8

A mixture of EXAMPLE 5 (255 mg) and $PtO_2$ (170 mg) in glacial acetic acid (2.5 mL) at 25° C. was stirred under hydrogen (1 atm) for 13 hours, treated with $PtO_2$ (60 mg), stirred under hydrogen for 24 hours, treated with ethyl acetate, filtered through diatomaceous earth (Celite®), concentrated, treated with ethyl acetate (80 mL), washed with 5% $Na_2CO_3$ and brine, dried ($Na_2SO_4$), filtered, concentrated, and flash chromatographed on silica gel with 96:3:1 dichloromethane/methanol/ammonium hydroxide.

EXAMPLE 9 and EXAMPLE 10

A mixture of EXAMPLE 6 (80 mg) and $PtO_2$ (160 mg) in glacial acetic acid (4 mL) at 25° C. was stirred under hydrogen (4 atm) for 18 hours, treated with $PtO_2$ (80 mg), stirred for 18 hours, treated with ethyl acetate, filtered through diatomaceous earth (Celite®), concentrated, treated with chloroform, washed with 5% $Na_2CO_3$ and brine, dried ($Na_2SO_4$), filtered, concentrated, and flash chromatographed on silica gel with 97:2:1 dichloromethane/methanol/ammonium hydroxide.

EXAMPLE 11

A mixture of EXAMPLE 8 (50 mg), formic acid (18.3 µL) and 37% aqueous formaldehyde (7 µL) in chloroform (1.5 mL) was stirred at 60° C. for 17 hours and cooled, treated with dichloromethane, washed with 5% $Na_2CO_3$ and brine, dried ($Na_2SO_4$), filtered, concentrated, and flash chromatographed on silica gel with 98:1:1 dichloromethane/methanol/ammonium hydroxide.

EXAMPLE 12

A mixture of EXAMPLE 7 (100 mg) and 37% aqueous formaldehyde (21 µL) in chloroform (2 mL) at 65° C. was stirred for 2 hours, treated with dichloromethane, washed with 5% $Na_2CO_3$ and brine, dried ($Na_2SO_4$), filtered, concentrated, and flash chromatographed on silica gel with 98.5:1:0.5 dichloromethane/methanol/ammonium hydroxide.

EXAMPLE 13

A mixture of EXAMPLE 7 (870 mg), triethylamine (367 mg), allyl acetate (315 mg), and tetrakis(triphenylphosphine)palladium(0) (280 mg) in toluene (15 mL) at 80° was stirred for 13 hours and cooled, concentrated, and flash chromatographed on silica gel with 98:1:1 dichloromethane/methanol/ammonium hydroxide.

EXAMPLE 14

A mixture of EXAMPLE 7 (75 mg), (2E)-3-(3-quinolinyl)-2-propenyl acetate (45 mg), and tetrakis(triphenylphosphine)palladium(0) (24 mg) in toluene (2 mL) was stirred at 25° C. for 18 hours, concentrated, and flash chromatographed on silica gel with 98:1:1 dichloromethane/methanol/ammonium hydroxide.

EXAMPLE 15

A mixture of (Z)-4-fluorobenzaldoxime (1 g) in DMF (6 mL) at 25° C. was treated with wet HCl gas from the head space of a concentrated HCl container (5 mL) then with N-chlorosuccinimde (960 mg) at a rate to maintain the solution temperature below 35° C., stirred at 25° C. for 15 minutes, treated with ethyl acetate, washed with water and brine, and dried ($Na_2SO_4$), filtered, and concentrated.

EXAMPLE 16

A mixture of EXAMPLE 13 (75 mg) and EXAMPLE 15 (54 mg), in benzene (15 mL) at 25° C. was treated with triethylamine (21 mg), stirred for 14 hours, treated with ethyl acetate, washed with 5% $Na_2CO_3$ and brine, dried ($Na_2SO_4$), filtered, concentrated, and flash chromatographed on silica gel with 98:1:1 dichloromethane/methanol/ammonium hydroxide.

EXAMPLE 17

A mixture of EXAMPLE 7 (50 g) and CBZ-NOS (19 g) in acetonitrile at 25° C. (1 mL) was stirred for 20 hours, treated with ethyl acetate, washed with 5% $Na_2CO_3$ and brine, dried ($Na_2SO_4$), filtered, concentrated, and flash chromatographed on silica gel with 1:1 acetone/hexanes.

ANALYTICAL DATA

EXAMPLE 3

$^{13}$C NMR (100 MHz, $CDCl_3$) δ 176.7, 109.5, 104.0, 99.2, 87.2, 84.5, 84.2, 79.4, 78.2, 73.3, 72.5, 70.0, 69.8, 66.2, 66.0, 49.5, 45.6, 44.9, 41.2, 40.7, 39.9, 38.2, 37.9, 36.5, 28.1, 26.3, 25.7, 23.7, 21.5, 21.2, 20.7, 18.5, 17.5, 15.0, 11.7, 10.3.

EXAMPLE 4

$^{13}$C NMR (100 MHz, CDCl$_3$) δ 176.7, 169.2, 168.7, 103.1, 102.6, 95.6, 94.5, 84.7, 84.1, 78.1, 77.5, 76.6, 75.1, 74.7, 74.0, 73.3, 72.8, 72.9, 70.7, 70.6, 69.5, 66.1, 65.6, 65.2, 49.4, 44.1, 43.5, 43.2, 43.0, 42.6, 40.7, 40.4, 37.9, 36.8, 36.3, 34.7, 34.5, 34.2, 31.5, 29.0, 28.8, 26.3, 25.3, 23.8, 23.6, 23.4, 21.6, 21.2, 20.9, 19.5, 19.2, 18.7, 17.7, 12.3, 11.6, 11.1, 10.1, 9.8.

EXAMPLE 5

$^{13}$C NMR (100 MHz, CDCl$_3$) δ 177.6, 164.1, 103.2, 94.1, 87.0, 82.8, 79.5, 77.8, 74.3, 73.7, 73.0, 70.5, 69.2, 65.9, 65.6, 49.5, 47.4, 47.0, 43.6, 43.4, 40.3, 37.8, 34.6, 34.1, 28.5, 27.8, 27.1, 24.3, 23.3, 21.6, 21.3, 17.9, 17.7, 11.6, 11.0, 10.5.

EXAMPLE 6

$^{13}$C NMR (100 MHz, CDCl$_3$) δ 174.9, 162.9, 105.2, 97.1, 84.7, 78.7, 77.7, 77.6, 75.0, 72.7, 70.5, 69.4, 66.0, 64.5, 49.3, 48.3, 48.0, 47.7, 42.3, 40.4, 36.3, 35.0, 34.4, 29.3, 26.5, 24.1, 23.8, 23.0, 21.4, 20.9, 17.4, 17.1, 15.7, 11.5, 10.3.

EXAMPLE 7

$^{13}$C NMR (100 MHz, CDCl$_3$) δ 177.2, 102.8, 95.1, 83.1, 81.9, 78.0, 77.6, 74.4, 73.2, 73.1, 70.9, 68.9, 65.7, 65.6, 49.4, 48.8, 46.6, 43.9, 43.0, 42.9, 40.9, 37.4, 34.8, 30.1, 28.9, 27.1, 23.8, 23.6, 22.1, 21.9, 21.6, 21.3, 17.9, 12.3, 11.1, 9.8.

EXAMPLE 8

$^{13}$C NMR (100 MHz, CDCl$_3$) δ 177.4, 102.3, 95.3, 85.3, 81.3, 77.9, 77.3, 75.0, 73.0, 72.8, 70.9, 69.4, 65.8, 65.2, 51.3, 49.3, 48.5, 44.4, 44.2, 41.2, 40.4, 39.3, 34.8, 30.1, 28.9, 25.8, 22.9, 21.7, 21.2, 20.9, 19.7, 19.3, 17.8, 13.4, 11.1, 10.5.

EXAMPLE 9

$^{13}$C NMR (100 MHz, CDCl$_3$) δ 177.7, 103.3, 95.0, 84.2, 83.4, 78.2, 77.1, 75.2, 72.9, 72.7, 70.6, 69.1, 65.7, 65.2, 52.5, 49.7, 49.4, 44.8, 43.9, 40.6, 40.3, 38.3, 34.8, 28.6, 27.3, 27.1, 25.0, 23.9, 21.9, 21.6, 21.2, 21.2, 18.0, 12.5, 11.3, 10.8.

EXAMPLE 10

$^{13}$C NMR (100 MHz, CDCl$_3$) δ 177.5, 103.3, 94.6, 83.6, 81.3, 78.2, 77.0, 74.8, 74.7, 72.9, 70.8, 69.0, 65.7, 65.3, 53.0, 49.5, 49.4, 45.6, 43.6, 42.3, 40.3, 34.7, 30.6, 28.8, 27.6, 22.0, 21.6, 21.3, 21.0, 19.7, 19.2, 18.2, 14.8, 11.1, 9.6.

EXAMPLE 11

$^{13}$C NMR (100 MHz, CDCl$_3$) δ 177.8, 102.3, 95.1, 85.6, 81.5, 77.8, 77.6, 75.4, 73.1, 72.9, 71.0, 69.3, 65.9, 65.2, 61.0, 55.4, 49.3, 44.4, 40.4, 40.3, 40.2, 37.7, 34.9, 29.1, 25.6, 23.0, 21.7, 21.3, 21.2, 20.2, 17.8, 13.3, 13.2, 11.2, 10.3.

EXAMPLE 12

$^{13}$C NMR (100 MHz, CDCl$_3$) δ 177.1, 102.5, 96.6, 82.9, 80.4, 77.97, 77.8, 76.5, 75.1, 74.6, 72.9, 71.1, 69.3, 66.3, 65.0, 50.7, 49.9, 49.4, 44.0, 43.5, 42.0, 40.5, 35.0, 31.9, 29.2, 25.4, 21.7, 21.2, 20.3, 20.1, 19.9, 17.9, 12.4, 12.0, 10.7.

EXAMPLE 13

$^{13}$C NMR (100 MHz, CDCl$_3$) δ 177.1, 135.9, 117.7, 103.3, 95.4, 83.1, 81.8, 78.1, 77.6, 77.2, 73.9, 73.8, 70.7, 69.0, 65.7, 65.5, 56.3, 54.3, 49.5, 48.6, 44.6, 43.4, 43.0, 40.4, 37.6, 34.8, 28.9, 26.0, 23.9, 23.4, 22.5, 21.7, 21.1, 17.9, 13.3, 11.2, 10.1.

EXAMPLE 14

$^{13}$C NMR (100 MHz, CDCl$_3$) δ 177.2, 149.9, 147.5, 131.8, 130.6, 129.9, 129.3, 129.1, 129.0, 128.1, 127.9, 126.8, 103.6, 95.7, 83.3, 81.7, 78.1, 77.7, 73.9, 73.0, 70.5, 69.2, 65.7, 65.6, 56.4, 53.7, 49.5, 49.2, 45.3, 43.7, 43.1, 40.4, 37.3, 34.8, 28.9, 25.9, 23.9, 23.7, 22.5, 21.7, 21.3, 17.9, 13.8, 13.4, 11.1, 10.6.

EXAMPLE 16

$^{13}$C NMR (100 MHz, CDCl$_3$) δ 177.1, 177.0, 165.3, 162.0, 156.8, 156.0, 128.8, 128.6, 126.1, 126.0, 115.8, 115.5, 103.6, 103.2, 96.2, 95.6, 83.4, 82.9, 81.8, 81.6, 80.5, 80.3, 78.4, 78.1, 78.1, 77.9, 77.2, 74.2, 74.1, 73.9, 73.8, 73.1, 72.9, 70.5, 70.4, 69.4, 69.1, 65.7, 65.6, 65.5, 57.3, 57.0, 55.4, 54.9, 52.5, 50.44, 50.41, 49.5, 46.0, 44.8, 43.8, 43.3, 43.1, 42.9, 40.3, 39.7, 38.9, 37.8, 37.7, 37.0, 28.8, 28.7, 26.3, 25.7, 25.5, 24.4, 23.9, 23.6, 23.5, 22.3, 21.6, 21.2, 20.9, 17.9, 14.6, 13.4, 11.1, 11.0, 10.9, 10.3, 10.2.

EXAMPLE 17

$^{13}$C NMR (100 MHz, CDCl$_3$) δ 176.7, 136.9, 128.4, 128.1, 127.7, 102.8, 95.0, 85.7, 83.4, 78.1, 77.7, 75.0, 73.6, 72.8, 70.8, 69.2, 66.9, 66.1, 65.2, 49.4, 49.0, 44.1, 42.3, 40.4, 34.6, 29.0, 26.4, 24.4, 23.9, 21.6, 21.2, 20.6, 17.8, 13.0, 11.1, 10.3.

The foregoing is merely illustrative of the invention and is not intended to limit the same to the disclosed compounds and processes. Variations and changes which are obvious to one skilled in the art are intended to be within the scope and nature of the invention as defined in the claims.

What is claimed is:

1. A compound, or a salt, thereof, having formula (I)

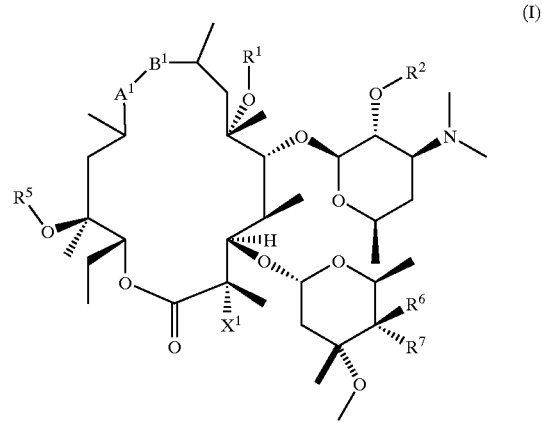

(I)

or formula (II)

-continued (II)

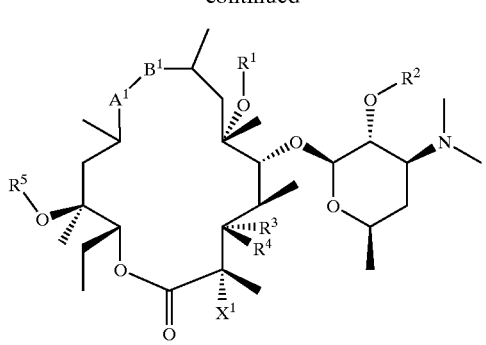

in which one of $A^1$ and $B^1$ is —$CH_2$—, and the other is —$N(R^8)$—;

$R^1$ is hydrogen, $C_1$-alkyl, or $R^9$;

$R^2$ is hydrogen or $R^P$, in which $R^P$ is a hydroxyl protecting moiety;

$R^3$ is hydrogen and $R^4$ is —OH, —$OR^{10}$, —$OC(O)R^{10}$, —$OC(O)NH_2$, —$OC(O)NHR^{11}$, —$OC(O)NR^{11}R^{12}$, —$OCH_2R^{13}$, —$OC(O)OCH_2R^{13}$, —$OC(O)NHCH_2R^{13}$, or —$OC(O)N(CH_2R^{13})_2$; or $R^3$ and $R^4$ together are =O;

$R^5$ is hydrogen, $R^{14}$, —$C(O)OR^{14}$, —$C(O)NH_2$, —$C(O)NHR^{15}$, —$C(O)NR^{15}R^{16}$, —$CH_2R^{17}$, —$C(O)OCH_2R^{17}$, —$C(O)NHCH_2R^{17}$, or —$C(O)N(CH_2R^{17})_2$;

one of $R^6$ or $R^7$ is hydrogen and the other is —OH, —$OR^{18}$, —$OC(O)R^{18}$, —$OC(O)OR^{18}$, —$OC(O)NH_2$, —$OC(O)NHR^{19}$, —$OC(O)NR^{19}R^{20}$, —$OCH_2R^{21}$, or —$OC(O)OCH_2R^{21}$; or $R^6$ and $R^7$ together are =O or —$CH_2O$—;

$R^8$ is hydrogen, $R^{22}$, —$C(O)OR^{22}$, —$C(O)NH_2$, —$C(O)NHR^{23}$, —$C(O)NR^{23}R^{24}$, —$CH_2R^{25}$, —$C(O)OCH_2R^{25}$, —$C(O)NHCH_2R^{25}$, or —$C(O)N(CH_2R^{25})_2$; or $R^1$ is $R^9$, and $R^8$ and $R^9$ together are —$CH_2$— or —$C(O)$—;

$R^{10}$, $R^{14}$, $R^{18}$, and $R^{22}$ are independently alkyl, —$(CH_2)$alkenyl, —$(CH_2)$alkynyl, alkyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, —$(CH_2)$alkenyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, or —$(CH_2)$alkynyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and $OR^{33}$;

$R^{11}$, $R^{12}$, $R^{15}$, $R^{16}$, $R^{19}$, $R^{20}$, $R^{23}$, and $R^{24}$, are independently alkyl, cycloalkyl, —$(CH_2)$alkenyl, —$(CH_2)$alkynyl, cycloalkyl, alkyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, —$(CH_2)$alkenyl substituted with one substituent selected from the group consisting of cycloalkyl, aryl, heteroaryl, heterocyclyl, —$NH_2$, —NH(alkyl), —NH$(alkyl)_2$, —OH, —O(alkyl), and —$OR^{33}$, or —$(CH_2)$alkynyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$; or $R^{11}$ and $R^{12}$ together, $R^{15}$ and $R^{16}$ together, $R^{19}$ and $R^{20}$ together, and $R^{23}$ and $R^{24}$ together are each independently $C_3$–$C_6$-alkylene, $C_5$–$C_6$-alkylene interrupted with one moiety selected from the group consisting of —O—, —NH—, —N(alkyl)-, —S—, —S(O)—, and —$SO_2$—, $C_3$–$C_6$-alkylene substituted with one substituent selected from the group consisting of —OH, —O(alkyl), —$OR^{33}$, =O, —$NH_2$, —NH(alkyl), and —$N(alkyl)_2$, or $C_5$–$C_6$-alkylene interrupted with one moiety selected from the group consisting of —O—, —NH—, —N(alkyl)-, —S—, —S(O)—, and —$SO_2$— and substituted with one substituent selected from the group consisting of aryl, heteroaryl, heterocyclyl, —OH, —O(alkyl), —$OR^{33}$, =O, —$NH_2$, —NH(alkyl), and —$N(alkyl)_2$;

$R^{13}$, $R^{17}$, $R^{21}$, and $R^{25}$ are independently alkyl interrupted with one or two or three moieties independently selected from the group consisting of —O—, —NH—, —N(alkyl)-, —S—, —S(O)—, and —$SO_2$— or alkyl interrupted with one or two or three moieties independently selected from the group consisting of —O—, —NH—, —N(alkyl)-, —S—, —S(O)—, and —$SO_2$— and substituted with one or two or three substituents independently selected from the group consisting of cycloalkyl, halo, aryl, heteroaryl, heterocyclyl —OH, —O(alkyl), —$OR^{33}$, =O, —$NH_2$, —NH(alkyl), and —$N(alkyl)_2$;

$R^{33}$ is alkyl substituted with one substituent selected from the group consisting of aryl, —OH, —O(alkyl), —S(alkyl), —S(O)(alkyl), and —$SO_2$(alkyl); and $X^1$ is hydrogen or fluoride.

2. The compound of claim 1 having formula (I) or formula (II), in which one of $A^1$ and $B^1$ is —$CH_2$—, and the other is —$N(R^8)$—; $R^1$ is hydrogen, $C_1$-alkyl, or $R^9$; $R^2$ is hydrogen or $R^P$, in which $R^P$ is a hydroxyl protecting moiety; $R^3$ is hydrogen and $R^4$ is —OH; or $R^3$ and $R^4$ together are =O; $R^5$ is hydrogen, $R^{14}$, —$C(O)OR^{14}$, —$C(O)NH_2$, —$C(O)NHR^{15}$, —$C(O)NR^{15}R^{16}$; one of $R^6$ or $R^7$ is hydrogen and the other is —OH; or $R^6$ and $R^7$ together are =O; $R^8$ is hydrogen, $R^{22}$, —$C(O)OR^{22}$, —$C(O)NH_2$, —$C(O)NHR^{23}$, or —$C(O)NR^{23}R^{24}$; or $R^1$ is $R^9$, and $R^8$ and $R^9$ together are —$CH_2$— or —$C(O)$—; $R^{14}$ and $R^{22}$ are independently alkyl, —$(CH_2)$alkenyl, —$(CH_2)$alkynyl, alkyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, —$(CH_2)$alkenyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, or —$(CH_2)$alkynyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$; $R^{15}$, $R^{16}$, $R^{23}$, and $R^{24}$ are independently alkyl, cycloalkyl, —$(CH_2)$alkenyl, —$(CH_2)$alkynyl, cycloalkyl, alkyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, —$(CH_2)$alkenyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —$OR^{33}$, or —$(CH_2)$alkynyl substituted with one substituent selected from the group consisting of cycloalkyl, aryl, heteroaryl, heterocyclyl, —$NH_2$, —NH(alkyl), —$NH(alkyl)_2$, —OH, —O(alkyl), and —OR$^{33}$; R$^{33}$ is alkyl substituted with one substituent selected from the group consisting of aryl, —OH, —O(alkyl), —S(alkyl), —S(O) (alkyl), and —SO$_2$ (alkyl); and X$^1$ is hydrogen or fluoride.

3. The compound of claim 2 having formula (I) or formula (II), in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen or R$^{14}$; one of R$^6$ or R$^7$ is hydrogen and the other is —OH; or R$^6$ and R$^7$ together are =O; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$) alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride.

4. The compound of claim 3 having formula (I) or formula (II), in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen or R$^{14}$; one of R$^6$ or R$^7$ is hydrogen and the other is —OH; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$) alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$) alkynyl substituted with one substituent selected from the group consisting of cycloalkyl, aryl, heteroaryl, and heterocyclyl; and X$^1$ is hydrogen or fluoride.

5. The compound of claim 4 having formula (I) or formula (II), in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; or R$^3$ and R$^4$ together are =O; R$^5$ is hydrogen or R$^{14}$; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$)alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$)alkynyl substituted with one substituent selected from the group consisting of cycloalkyl, aryl, heteroaryl, and heterocyclyl; and X$^1$ is hydrogen or fluoride.

6. The compound of claim 5 having formula (I) or formula (II), in which one of A$^1$ and B$^1$ is —CH$_2$—, and the other is —N(R$^8$)—; R$^1$ is hydrogen, C$_1$-alkyl, or R$^9$; R$^2$ is hydrogen or R$^P$, in which R$^P$ is a hydroxyl protecting moiety; R$^3$ is hydrogen and R$^4$ is —OH; R$^5$ is hydrogen or R$^{14}$; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{14}$ and R$^{22}$ are independently alkyl, —(CH$_2$) alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$) alkynyl substituted with one substituent selected from the group consisting of cycloalkyl, aryl, heteroaryl, and heterocyclyl; and X$^1$ is hydrogen or fluoride.

7. The compound of claim 6 having formula (I) or formula (II), in which one of A$^1$ and B$^1$ is —CH$_2$—, and the other is —N(R$^8$)—; R$^1$ is hydrogen or R$^9$; R$^2$ is hydrogen or R$^P$, in which R$^P$ is a hydroxyl protecting moiety; R$^3$ is hydrogen and R$^4$ is —OH; R$^5$ is hydrogen; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{22}$ is alkyl, —(CH$_2$) alkenyl, —(CH$_2$)alkynyl, alkyl substituted with one substituent selected from the group consisting of cycloalkyl, aryl, heteroaryl and heterocyclyl, —(CH$_2$)alkenyl substituted with one substituent selected from the group consisting of cycloalkyl, aryl, heteroaryl and heterocyclyl, or —(CH$_2$) alkynyl substituted with one substituent selected from the group consisting of cycloalkyl, aryl, heteroaryl, and heterocyclyl; and X$^1$ is hydrogen or fluoride.

8. The compound of claim 7 having formula (I) or formula (II), in which one of A$^1$ and B$^1$ is —CH$_2$—, and the other is —N(R$^8$)—; R$^1$ is hydrogen or R$^9$; R$^2$ is hydrogen or R$^P$, in which R$^P$ is a hydroxyl protecting moiety; R$^3$ is hydrogen and R$^4$ is —OH; R$^5$ is hydrogen; R$^6$ is hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{22}$ is alkyl, —(CH$_2$) alkenyl, alkyl substituted with one substituent selected from the group consisting of aryl, heteroaryl, and heterocyclyl, or —(CH$_2$)alkenyl substituted with one substituent selected from the group consisting of aryl and heteroaryl; and X$^1$ is hydrogen or fluoride.

9. The compound of claim 8 having formula (I) or formula (II), in which one of A$^1$ and B$^1$ is —CH$_2$—, and the other is —N(R$^8$)—; R$^1$ is hydrogen or R$^9$; R$^2$ is hydrogen or R$^P$, in which R$^P$ is a hydroxyl protecting moiety; R$^3$is hydrogen and R$^4$ is —OH; R$^5$ is hydrogen; R$^6$ is hydrogen; R$^7$ is —OH; R$^8$ is hydrogen, methyl, ethyl, phenylmethyl, (pyridin-3-yl)methyl, prop-2-enyl, 3-(quinolin-3-yl)-prop-2-enyl, 3-(isoquinolin-3-yl)-prop-2-enyl, 3-(5-(2-methyl-2H-tetrazol-5-yl)-thien-2-yl)-prop-2-enyl, 3-(5-(pyrimidin-2-yl)-thien-2-yl)-prop-2-enyl, 3-(5-(pyridin-2-yl)-thien-2-yl)-prop-2-enyl, (3-(4-fluorophenyl)-4,5-dihydroisoxazol-5-yl) methyl, (3-(phenyl)-4,5-dihydroisoxazol-5-yl)methyl, (3-(pyridin-2-yl)-4,5-dihydroisoxazol-5-yl)methyl, or (phenylmethoxy)carbonyl; or R$^1$ is R$^9$, and R$^8$ and R$^9$ together are —CH$_2$—; and X$^1$ is hydrogen or fluoride.

10. The compound of claim 1 having formula (I) in which one of A$^1$ and B$^1$ is —CH$_2$—, and the other is —N(R$^8$)—; R$^1$ is hydrogen or R$^9$; R$^2$, R$^5$, and R$^6$ are hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{22}$ is alkyl, —(CH$_2$) alkenyl, alkyl substituted with one substituent selected from the group consisting of phenyl and 4,5-dihydroisoxazolyl, in which the 4,5-dihydroisoxazolyl is substituted with phenyl, and the phenyl is further substituted with one halo substituent, or —(CH$_2$)alkenyl substituted with pyridyl, in which the pyridyl is fused with phenyl; and X$^1$ is hydrogen.

11. The compound of claim 1 having formula (I) in which one of A$^1$ and B$^1$ is —CH$_2$—, and the other is —N(R$^8$)—; R$^1$ is hydrogen or R$^9$; R$^2$, R$^5$, and R$^6$ are hydrogen; R$^7$ is —OH; R$^8$ is hydrogen, R$^{22}$, or —C(O)OR$^{22}$; or R$^1$ is R$^9$, and R$^8$ and R$^9$ together are —CH$_2$—; R$^{22}$ is C$_1$-alkyl, —(CH$_2$)—C$_2$-alkenyl, C$_1$-alkyl substituted with one substituent selected from the group consisting of phenyl and 4,5-dihydroisoxazolyl, in which the 4,5-dihydroisoxazolyl is substituted with phenyl, and the phenyl is further substituted with one halo substituent, or —(CH$_2$)—C$_2$-alkenyl substituted with pyridyl, in which the pyridyl is fused with phenyl; and X$^1$ is hydrogen.

12. The compound of claim 11 in which A$^1$ is —N(R$^8$)—, B$^1$ is —CH$_2$—; R$^1$, R$^2$, R$^5$, and R$^6$ are hydrogen; R$^7$ is —OH; R$^8$ is hydrogen, methyl, prop-2-enyl, (3-(4-fluorophenyl)-4,5-dihydroisoxazol-5-yl)methyl, 3-(quinolin-3-yl)-prop-2-enyl, or (phenylmethyoxy)carbonyl; and X$^1$ is hydrogen.

13. The compound of claim 11 in which A$^1$ is —CH$_2$—, B$^1$ is —N(R$^8$)—; R$^1$, R$^2$, R$^5$, and R$^6$ are hydrogen; R$^7$ is —OH; R$^8$ is hydrogen, methyl, prop-2-enyl, (3-(4-fluorophenyl)-4,5-dihydroisoxazol-5-yl)methyl, 3-(quinolin-3-yl)-prop-2-enyl, or (phenylmethyoxy)carbonyl; and X$^1$ is hydrogen.

14. The compound of claim 11 in which one of A$^1$ and B$^1$ is —CH$_2$—, and the other is —N(R$^8$)—; R$^1$ is R$^9$; R$^2$, R$^5$, and R$^6$ are hydrogen; R$^7$ is —OH; R$^8$ and R$^9$ together are —CH$_2$—; and X$^1$ is hydrogen.

15. A composition for treatment of bacterial infections in a fish or a mammal comprising a therapeutically effective amount of a compound of claim 1.

16. A method for treatment of bacterial infections in a fish or a mammal comprising administering to the fish or the mammal a therapeutically effective amount of a compound of claim 1.

17. A compound of claim 1, or a therapeutically acceptable salt thereof, which is (2R,3S,5S,8R,10S,11R,12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S,14R)-6-allyl-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S,14R)-2-ethyl-3,10-dihydroxy-3,5,8,10,12,14-hexamethyl-15-oxo-6-((2E)-3-quinolin-3-ylprop-2-enyl)-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S,14R)-2-ethyl-6-((3-(4-fluorophenyl)-4,5-dihydroisoxazol-5-yl)methyl)-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

benzyl (2R,3S,5S,8R,10S,11R,12S,13S,14R)-13-((2,6-dideoxy-3-C-methyl-3-O-methyl-α-L-ribo-hexopyranosyl)oxy)-2-ethyl-3,10-dihydroxy-3,5,8,10,12,14-hexamethyl-15-oxo-11-((3,4,6-trideoxy-3-(dimethylamino)-β-D-xylo-hexopyranosyl)-oxy)-1-oxa-6-azacyclopentadecane-6-carboxylate;

(2S,4S,5R,8R,9S,10S,11R,12R,14R)-5-ethyl-4-hydroxy-2,4,8,10,12,14-hexamethyl-7-oxo-11-((3,4,6-trideoxy-3-(dimethylamino)-β-D-xylo-hexopyranosyl)oxy)-6,17-dioxa-1-azabicyclo(10.3.2)heptadec-9-yl 2,6-dideoxy-3-C-methyl-3-O-methyl-α-L-ribo-hexopyranoside;

(2R,3S,5S,8S,10S,11R,12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8S,10S,11R,12S,13S,14R)-2-ethyl-3,10-dihydroxy-3,5,6,8,10,12,14-heptamethyl-15-oxo-11-((3,4,6-trideoxy-3-(dimethylamino)-β-D-xylo-hexopyranosyl)oxy)-1-oxa-6-azacyclopentadecan-13-yl 2,6-dideoxy-3-C-methyl-3-O-methyl-α-L-ribo-hexopyranoside;

(2R,3S,5S,8R,10S,11R,12S,13S,14R)-2-ethyl-3,10-dihydroxy-3,5,8,10,12,14-hexamethyl-15-oxo-11-((3,4,6-trideoxy-3-(dimethylamino)-β-D-xylo-hexopyranosyl)oxy)-1-oxa-7-azacyclopentadecan-13-yl 2,6-dideoxy-3-C-methyl-3-O-methyl-α-L-ribo-hexopyranoside; or (2R,3S,5R,8S,10S,11R,12S,13S,14R)-2-ethyl-3,10-dihydroxy-3,5,8,10,12,14-hexamethyl-15-oxo-1-((3,4,6-trideoxy-3-(dimethylamino)-β-D-xylo-hexopyranosyl)oxy)-1-oxa-7-azacyclopentadecan-13-yl 2,6-dideoxy-3-C-methyl-3-O-methyl-α-L-ribo-hexopyranoside.

* * * * *

UNITED STATES PATENT AND TRADEMARK OFFICE
CERTIFICATE OF CORRECTION

PATENT NO. : 6,933,283 B2
DATED : August 23, 2005
INVENTOR(S) : Richard Clark et al.

It is certified that error appears in the above-identified patent and that said Letters Patent is hereby corrected as shown below:

Column 28,
Line 41, replace "15-oxo-1-((3,4,6-" with -- 15-oxo-11-((3,4,6- --.

Signed and Sealed this

Fourteenth Day of March, 2006

JON W. DUDAS
*Director of the United States Patent and Trademark Office*